(12) United States Patent
Balicki et al.

(10) Patent No.: US 9,815,206 B2
(45) Date of Patent: Nov. 14, 2017

(54) SURGICAL SYSTEM USER INTERFACE USING COOPERATIVELY-CONTROLLED ROBOT

(71) Applicant: The Johns Hopkins University, Baltimore, MD (US)

(72) Inventors: Marcin A. Balicki, Baltimore, MD (US); Peter Kazanzides, Towson, MD (US); Anton Deguet, Idlewylde, MD (US); Russell H. Taylor, Severna Park, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 141 days.

(21) Appl. No.: 14/497,178

(22) Filed: Sep. 25, 2014

(65) Prior Publication Data

US 2016/0089212 A1 Mar. 31, 2016

(51) Int. Cl.
*G06F 19/00* (2011.01)
*B25J 13/00* (2006.01)
(Continued)

(52) U.S. Cl.
CPC ......... *B25J 13/003* (2013.01); *A61B 19/2203* (2013.01); *A61B 19/5202* (2013.01); *A61B 19/5212* (2013.01); *A61B 19/5223* (2013.01); *A61B 19/56* (2013.01); *B25J 13/02* (2013.01); *B25J 13/04* (2013.01); *B25J 13/06* (2013.01); *B25J 13/065* (2013.01); *G06F 3/0338* (2013.01); *G06F 3/0346* (2013.01); *G06F 3/0362* (2013.01); *G06F 3/03545* (2013.01); *G06F 3/0482* (2013.01);
(Continued)

(58) Field of Classification Search
USPC .................................. 700/245–264
See application file for complete search history.

(56) References Cited

U.S. PATENT DOCUMENTS 5,784,542 A * 7/1998 Ohm ..................... B25J 3/04
700/247
7,206,626 B2 * 4/2007 Quaid, III ............. A61B 90/36
600/407
(Continued)

OTHER PUBLICATIONS

International Search Report and Written Opinion in International Application No. PCT/US2015/051907 dated Jan. 4, 2016.

*Primary Examiner* — Bhavesh V Amin
(74) *Attorney, Agent, or Firm* — Venable LLP; Henry J. Daley; Laura G. Remus

(57) ABSTRACT

According to some embodiments of the present invention, a cooperatively controlled robot includes a robotic actuator assembly comprising a tool holder and a force sensor, a control system adapted to communicate with the robotic actuator assembly and the force sensor, and an output system in communication with the control system. The tool holder is configured to receive a tool to be manipulated by a user. The control system is configured to receive an instruction from a user to switch from a robot control mode into a user interface control mode. The force sensor is configured to measure at least one of a force and a torque applied to the tool, and the control system is configured to receive an indication of the at least one of a force and a torque applied to the tool and manipulate the output system based on the indication.

20 Claims, 7 Drawing Sheets

(51) Int. Cl.
*A61B 19/00* (2006.01)
*B25J 13/04* (2006.01)
*B25J 13/06* (2006.01)
*B25J 13/02* (2006.01)
*G06F 3/0346* (2013.01)
*G06F 3/0338* (2013.01)
*G06F 3/0482* (2013.01)
*G06F 3/0362* (2013.01)
*G06F 3/0354* (2013.01)

(52) U.S. Cl.
CPC ............ *A61B 2019/2296* (2013.01); *A61B 2019/4836* (2013.01); *A61B 2019/568* (2013.01); *Y10S 901/06* (2013.01)

(56) References Cited

U.S. PATENT DOCUMENTS

| | | | |
|---|---|---|---|
| 7,379,541 B2 | 5/2008 | Iggulden et al. | |
| 7,689,320 B2 * | 3/2010 | Prisco | A61B 1/00193 318/568.11 |
| 8,398,541 B2 | 3/2013 | DiMaio et al. | |
| 8,527,094 B2 * | 9/2013 | Kumar | A61B 19/22 600/101 |
| 2002/0003528 A1 * | 1/2002 | Rosenberg | G06F 3/016 345/157 |
| 2002/0151784 A1 * | 10/2002 | Mizoguchi | G02B 21/0012 600/407 |
| 2004/0106916 A1 * | 6/2004 | Quaid | G02B 21/0012 606/1 |
| 2004/0243147 A1 * | 12/2004 | Lipow | A61B 90/36 606/130 |
| 2005/0029978 A1 * | 2/2005 | Oleynikov | A61B 1/041 318/568.12 |
| 2005/0267826 A1 * | 12/2005 | Levy | B25J 9/1689 705/34 |
| 2005/0288819 A1 * | 12/2005 | de Guzman | F16L 55/32 700/245 |
| 2006/0142657 A1 * | 6/2006 | Quaid | A61B 17/1764 600/424 |
| 2006/0149418 A1 * | 7/2006 | Anvari | A61G 13/10 700/245 |
| 2007/0083098 A1 * | 4/2007 | Stern | A61B 1/00188 600/407 |
| 2007/0156157 A1 | 7/2007 | Nahum et al. | |
| 2008/0010706 A1 * | 1/2008 | Moses | 600/407 |
| 2008/0033240 A1 | 2/2008 | Hoffman et al. | |
| 2009/0036902 A1 * | 2/2009 | DiMaio | A61B 8/12 606/130 |
| 2009/0326322 A1 * | 12/2009 | Diolaiti | A61B 1/00039 600/112 |
| 2010/0145520 A1 * | 6/2010 | Gerio | B25J 13/06 700/264 |
| 2010/0152899 A1 * | 6/2010 | Chang | B25J 9/162 700/262 |
| 2010/0164950 A1 * | 7/2010 | Zhao | G06T 7/0075 345/419 |
| 2010/0225209 A1 * | 9/2010 | Goldberg | A61B 19/2203 312/209 |
| 2010/0280663 A1 * | 11/2010 | Abdallah | H01R 13/17 700/264 |
| 2010/0318099 A1 * | 12/2010 | Itkowitz | A61B 19/2203 606/130 |
| 2011/0208355 A1 * | 8/2011 | Tsusaka | B25J 9/1664 700/246 |
| 2011/0213384 A1 * | 9/2011 | Jeong | A61B 19/2203 606/130 |
| 2011/0288684 A1 * | 11/2011 | Farlow | B25J 11/009 700/264 |
| 2012/0053597 A1 * | 3/2012 | Anvari | B25J 9/1689 606/130 |
| 2012/0071752 A1 * | 3/2012 | Sewell | A61B 6/12 600/424 |
| 2013/0131867 A1 | 5/2013 | Olds et al. | |
| 2013/0178868 A1 * | 7/2013 | Roh | A61B 19/2203 606/130 |
| 2014/0052150 A1 | 2/2014 | Taylor et al. | |
| 2014/0094968 A1 | 4/2014 | Taylor et al. | |
| 2014/0330288 A1 * | 11/2014 | Date | A61B 19/2203 606/130 |

* cited by examiner

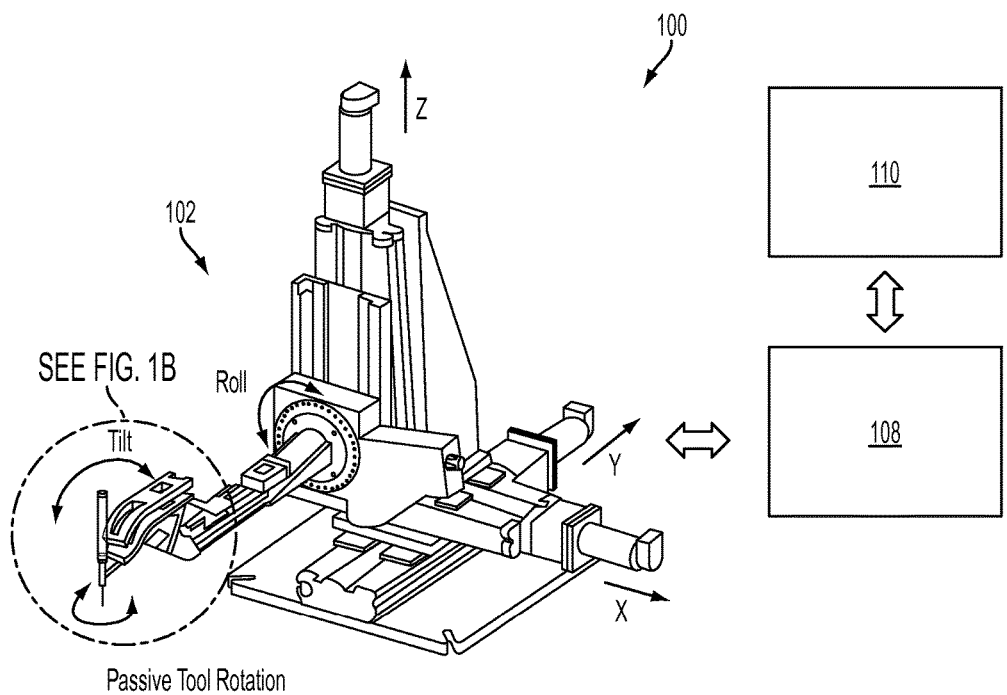
FIG. 1A
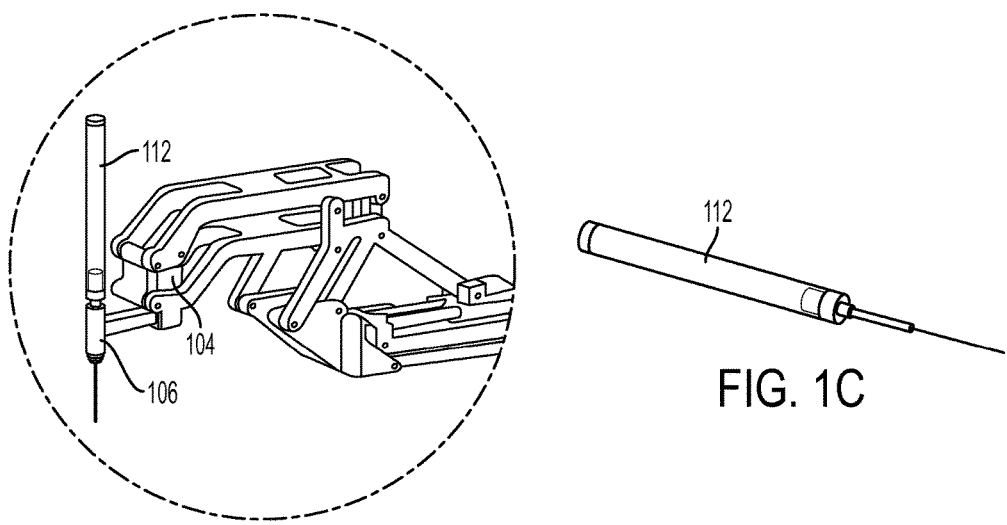
FIG. 1B
FIG. 1C

SURGICAL SYSTEM USER INTERFACE USING COOPERATIVELY-CONTROLLED ROBOT

This invention was made with Government support of Grant No. 1R01 EB 007969-01, awarded by the Department of Health and Human Services, the National Institutes of Health (NIH), and with Government support of Grant No. EEC-9731478, awarded by the National Science Foundation. The U.S. Government has certain rights in this invention.

BACKGROUND

1. Technical Field

The field of the currently claimed embodiments of this invention relates to robotic systems, and more particularly to a surgical system user interface using cooperative control robotic systems and robotic systems that include the user interface.

2. Discussion of Related Art

Surgeons and operating room staff interact directly with computer integrated surgical equipment through pedals, physical knobs, touch panels, and occasionally through voice commands. In most surgical scenarios, surgeons handle surgical instruments manually and may not be able to directly change system parameters located on remote interfaces (e.g., touch panels) due to sterility requirements or because their hands are occupied. Instead they communicate the necessary settings to an assistant who adjusts the parameters as requested. This exchange adds to operation time and can inadvertently cause harm to the patient if there is a miscommunication.

Additionally, for an efficient inspection of pre-operative surgical plans or diagnostic images during the operation, a complex control interface such as a three degrees-of-freedom (DOF) or six DOF joystick may be required.

The addition of complex surgical devices into the operating room introduces more physical interfaces that compete for limited space. Minimizing the number of these interfaces is desirable.

SUMMARY

According to some embodiments of the present invention, a cooperatively controlled robot includes a robotic actuator assembly comprising a tool holder and a force sensor, a control system adapted to communicate with the robotic actuator assembly and the force sensor, and an output system in communication with the control system. The tool holder is configured to receive a tool to be manipulated by a user. The control system is configured to receive an instruction from a user to switch from a robot control mode into a user interface control mode. The force sensor is configured to measure at least one of a force and a torque applied to the tool, and the control system is configured to receive an indication of the at least one of a force and a torque applied to the tool and manipulate the output system based on the indication.

According to some embodiments of the present invention, a surgical system user interface for a cooperatively controlled robot includes a control system adapted to communicate with a robotic actuator assembly and a force sensor, and an output system in communication with the control system. The control system is configured to receive an instruction from a user to switch from a robot control mode into a user interface control mode, and the control system is configured to receive from a force sensor an indication of at least one of a force and a torque applied to a tool and manipulate the output system based on the indication.

BRIEF DESCRIPTION OF THE DRAWINGS

Further objectives and advantages will become apparent from a consideration of the description, drawings, and examples.

FIG. 1A is schematic illustration of a cooperatively-controlled robot according to an embodiment of the invention;

FIG. 1B shows a robotic actuator assembly including a force sensor and a tool holder;

FIG. 1C shows a schematic illustration of a tool according to an embodiment of the invention;

DETAILED DESCRIPTION

Figure 2:
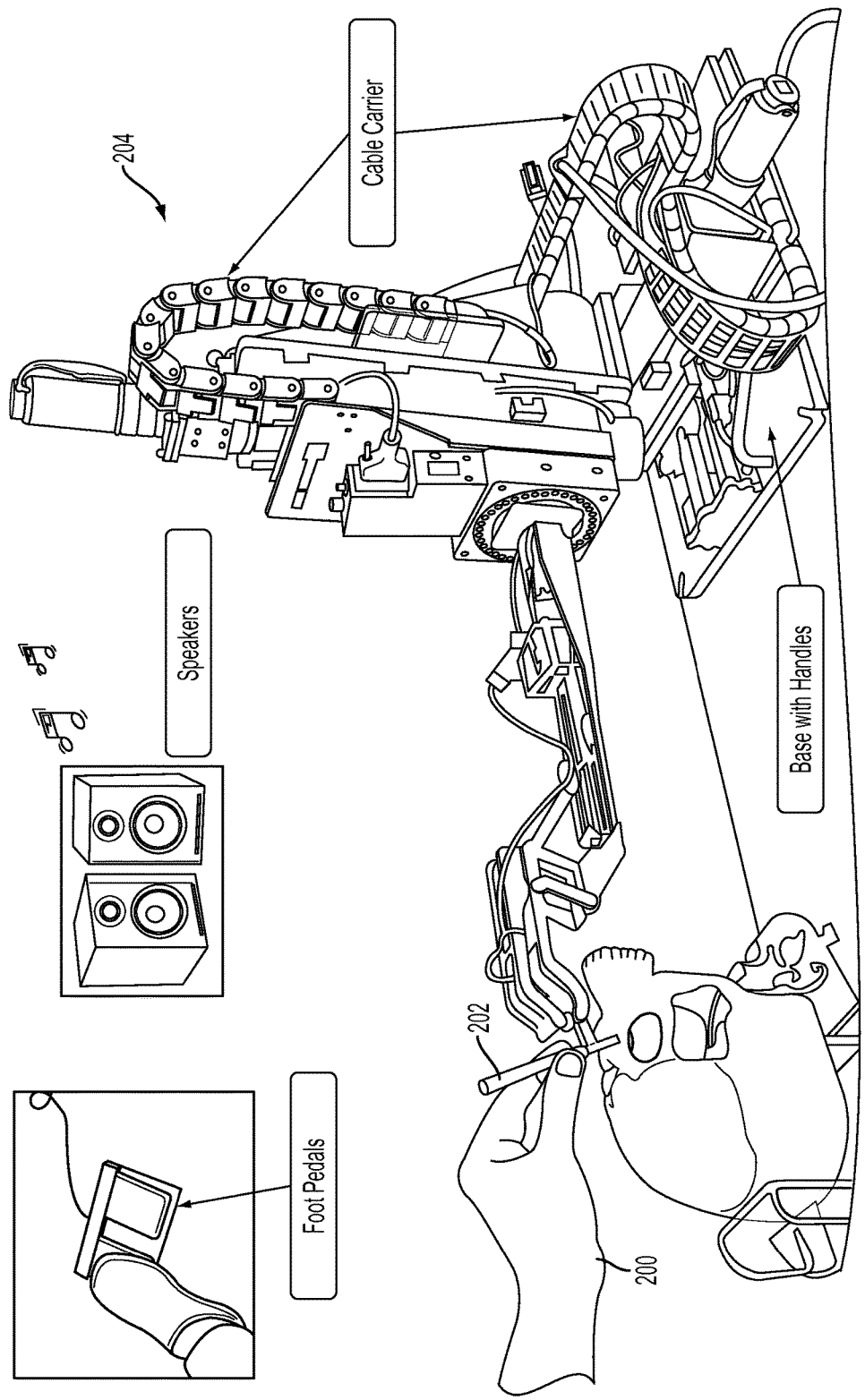
FIG. 2 shows a user interacting with the cooperatively controlled robot.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

FIG. 1A is a schematic illustration of a cooperatively controlled robot according to an embodiment of the invention. The cooperatively controlled robot 100 includes a robotic actuator assembly 102 comprising a tool holder 106 and a force sensor 104, as shown in FIG. 1B. The cooperatively controlled robot 100 also includes a control system 108 adapted to communicate with the robotic actuator assembly 102 and force sensor 104, and an output system 110 in communication with the control system 108. The tool holder 106 is configured to receive a tool 112 to be held by a surgeon. FIG. 1C shows a schematic illustration of the tool 112. The control system 108 is configured to receive an instruction from a user to switch from a robot control mode into a user interface control mode. The force sensor 104 is configured to measure at least one of a force and a torque applied to the tool 112, and the control system 108 is configured to receive an indication of the at least one of a force and a torque applied to the tool 112 and manipulate the output system 110 based on the indication. According to some embodiments of the invention, the output system is a visual display system, an audio display system, a microscope, a light source, or a second robotic actuator assembly.

The term "cooperative control" is intended to refer to a robotic system in which the user interacts directly with at least a portion of the robotic actuator assembly so that the robot effectively assists the user in performing certain operations. In this case, the user is located in close proximity to the robotic actuator assembly. FIG. 2 shows one possible example in which the user 200 grabs a tool 202 that is attached to the robotic actuator assembly 204. The motion of the tool 202, for example, is then a result of cooperative actions by both the user 200 and the robot.

The cooperatively controlled robot and surgical system user interface described herein allows for dual use of the robot. By halting the motion of the robot, the forces applied by the surgeon on the tool handle can be interpreted as though the tool were a velocity or position based multi-axis joystick. The general concept is similar to the finger joystick controller integrated in the IBM ThinkPad. However, the input in the present system is also a surgical instrument, and includes additional degrees of freedom. Additionally, the robot may provide haptic feedback to the user, and the system may be combined with a variety of devices and software applications.

The cooperatively controlled robot in the user interface mode may include a velocity control mode, in which the numeric output (e.g., x, y velocity) used for surgical system user interfaces changes proportionally to the force/torque applied to the tool. For example, a 2-D mouse cursor can be manipulated on a 2-D plane by controlling the cursor's x and y velocity with 2-D force exerted on the tool. This can be extended to any number of degrees of freedom. The relationship between the force/torque and the numeric output may be linear, non-linear (e.g., exponential), time-based, or context-based (e.g., having a low conversion factor when the cursor is located above a widget, and a high conversion factor when it is off the widget.)

The cooperatively controlled robot in the user interface mode may allow for position control, in which the numeric output (e.g., x, y position) used for surgical system user interfaces is proportional to the force/torque applied to the tool. For example, the force/torque applied to the tool is translated into an output position, such as a displacement from the origin. Once the user releases the instrument (force/torque=0, the position returns to origin. The relationship between the force/torque and the numeric output cold be linear, non-linear (e.g., exponential), time-based, or context-based (e.g., having a low conversion factor when the cursor is located above a widget, and a high conversion factor when it is off the widget.)

The cooperatively controlled robot in the user interface mode may act as a single axis selector. In this mode the position or velocity control methods described above may be applied to enable the tool to behave like a knob. For example, a torque may be applied by the user to the tool to cycle through a list of system options. According to some embodiments of the invention, a user may acknowledge a system notification or answer a question by applying a force/torque to the tool to select one of the options. For example, in response to the question "Shall we proceed?" the user may turn the tool clockwise to select "yes," and counterclockwise to select "no."

The cooperatively controlled robot in the user interface mode may be used to generate a button press function. The event is generated when the user exerts a force on the tool along a predefined axis for a given duration, and/or force magnitude. For example, if the system is in a 2-D user interface mode, exerting a force on the tool along the direction normal to the plane of 2-D motion creates a button press event. Another button press application is an item selection acknowledgement in the in the single axis selector mode where the force is applied along the selection axis.

The cooperatively controlled robot in the user interface mode may allow the user to zoom in and out. If the system is in a 2-D mode, pressing or pulling along the direction normal to the plane of 2-D motion causes the view/screen to zoom in and out.

The additional feedback methods that complement the above functions include graphical, haptic and audio feedback. Graphical feedback could include size and color modulation of the graphical items the input cursor is moving or hovering over. To provide haptic feedback the robot may vibrate the tool slightly (e.g., induce sinusoidal motion) when a button press is initiated, or if the pointer travels over a visual widget. To provide audio feedback, the user input events can be complimented by corresponding audio signals, e.g., a beep for a selection.

The cooperatively controlled robot in the user interface mode may have a variety of modes. A 1-D mode may be activated in which the cooperatively controlled robot is used as an option selector, for example. A 2-D mode may be used to control planar mouse motion, or as a 2-D option selector. A 2-D+ system may include the functions of the 2-D system but also allow for button input. A 2-D+ system may also allow for torque-based rotation about the z-axis, as well as zoom capability based on force exerted along the z-axis. In a 3-D mode forces on the tool may be translated into pointer motion in three DOF, or may change the view of a 3-D model. This may include a zoom function. A 6-D mode may employ full six DOF joystick control.

The cooperatively controlled robot may be used for a variety of applications including, but not limited to, controlling a mouse pointer on a display screen, controlling a set of system options, answering aural or visual prompts, acknowledging system notifications, controlling an actuated microscope/endoscope/tissue retractor, inspecting patient data/images, and controlling an auxiliary robot.

The following examples describe some embodiments in more detail. The broad concepts of the current invention are not intended to be limited to the particular examples.

The EyeRobot is an example of a cooperatively controlled robot in which the surgeon and robot share the control of the surgical instrument (see FIGS. 1A and 2). The robot senses the forces (via a 6-DOF force/torque sensor) exerted by the operator on the surgical instrument handle and moves the instrument to comply. Through this partnership, the surgeon is directly controlling the instrument that is used to operate on the patient and the surgeon's physiological hand tremor is significantly reduced. The combination provides the precision and sensitivity of a machine with the manipulative simplicity, immediacy and the natural hand-eye coordination of hand-held tools to which the surgeon is already accustomed.

The 6-DOF force/torque (FT) sensor on the EyeRobot is predominantly used for controlling the motion of the surgical instrument. The deflection of the actual tool from physical user input when the robot is not moving is minimal due to a very stiff structural design and non-backdrivable nature of the actuators. When the robot is not being commanded to move, the FT sensor can also be repurposed on-the-fly to provide an intuitive and instant user input method for interaction with the rest of the surgical system.

Figure 3:
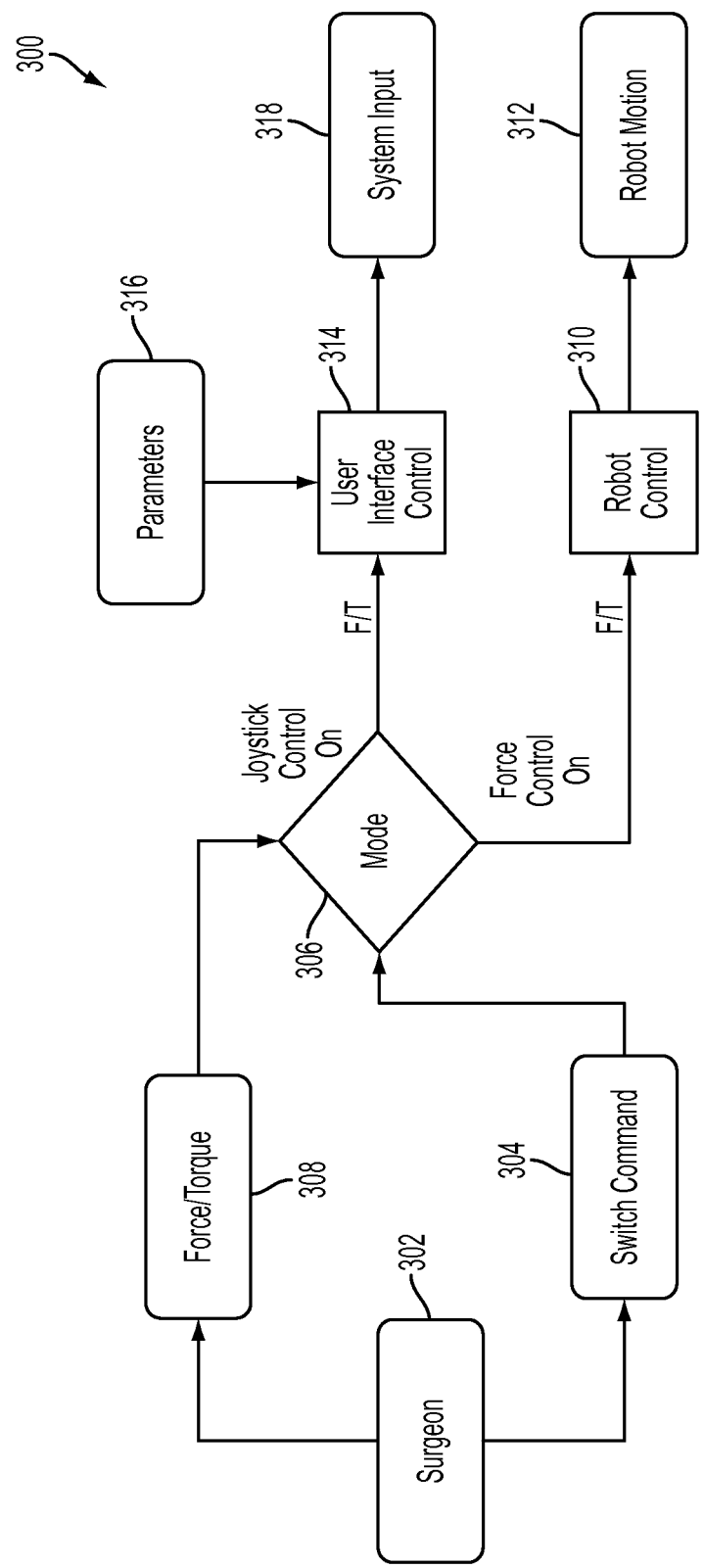
FIG. 3 shows a flow diagram for a surgeon controlling the cooperatively controlled robot according to an embodiment of the invention.

FIG. 3 shows a flow diagram 300 for a surgeon 302 controlling the cooperatively controlled robot. The surgeon 302 can instruct the cooperatively controlled robot to switch between a robot control mode and a user interface control mode. The switch command 304 may be made by engaging a physical button or a foot pedal, by a voice command detected by microphone, via a graphical user interface (GUI) button on a second display system such as a nurse's console, or automatically by the surgical system based on the context of the procedure or internal system event. The switch command 304 controls the mode 306 and determines how the system will respond to a force/torque 308 applied to the force sensor. When the cooperatively controlled robot is in the robot control mode 310, the applied forces/torques 308 control the robot's motion 312. When the surgical system is in the user interface control mode 314, the applied forces/torques 308 are used to select parameters 316 that act as system input 318. The robot's motion is disabled, and one or more of the modes described below is enabled.

Figure 4:
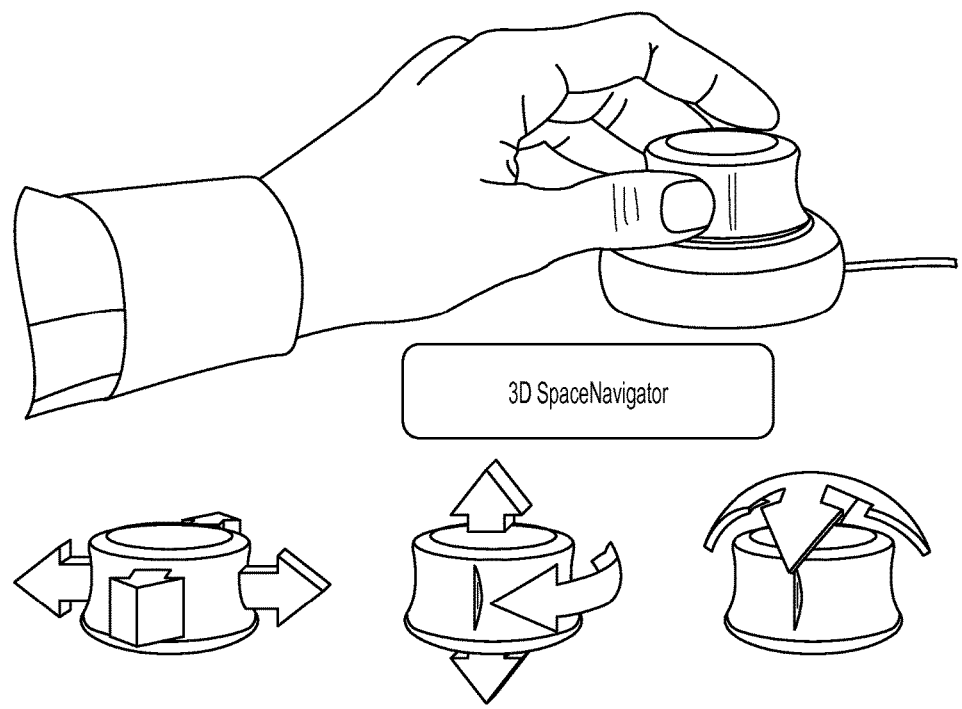
FIG. 4 shows a commercial 3D SpaceNavigator (3Dconnexion, Inc.)

Another option is to insert a special joystick tool into the tool adapter. This tool does not have a standard length tool shaft to prevent accidental collisions with the anatomy. When its insertion is detected (e.g., via a contact switch), the joystick mode is enabled. Furthermore, this tool could constrain the rotation about the tool axis so that torques can be detected by the force/torque sensor to provide full 6-DOF input. The force/torque on the surgical tool or special joystick can be interpreted as for a 6-DOF rate control joystick, much like the commercial 3D SpaceNavigator (3Dconnexion, Inc.) shown in FIG. 4.

Figure 5:
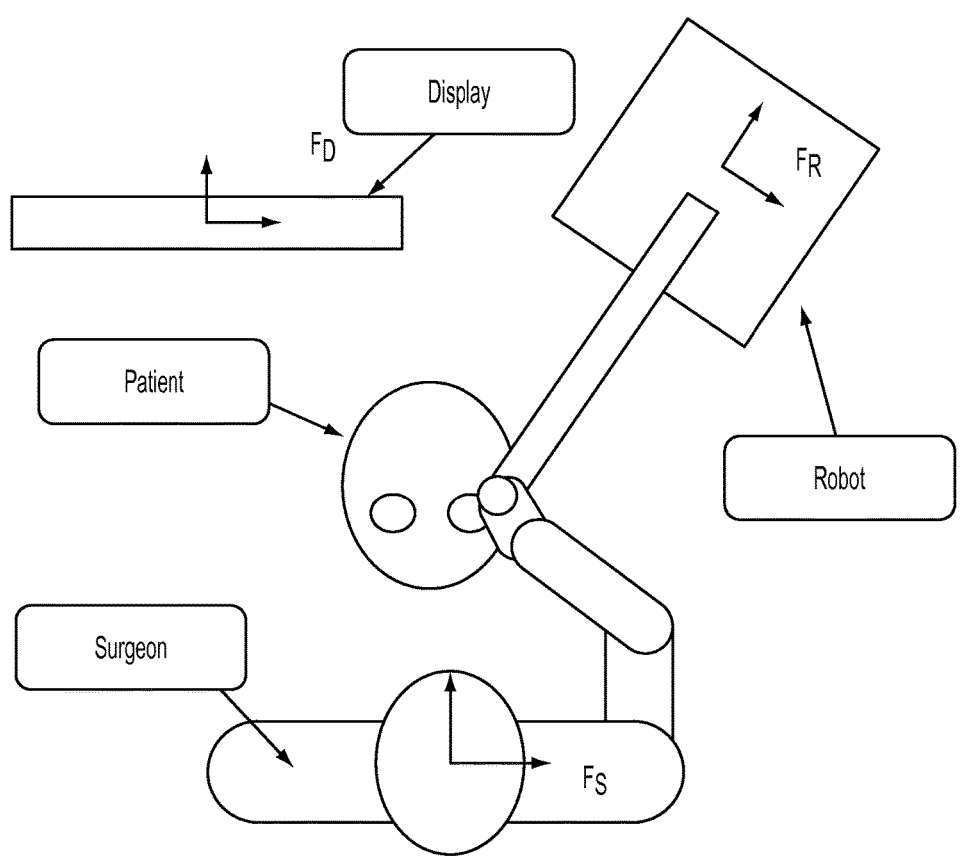
FIG. 5 illustrates the relationship between the robot frame ($F_R$) and the surgeon's body frame ($F_S$)

Although the force/torque measured in the tool or robot coordinate frame can be used directly for user interface operation, it is not always intuitive to the user to do so. According to some embodiments of the invention, the force/torque measurement frame (often located in the robot frame ($F_R$)) is aligned with the surgeon's body frame ($F_S$). The frames $F_R$ and $F_S$ are shown in FIG. 5. This example robot-surgeon arrangement has the effect of rotating the handle forces in the robot frame by ±30° about the robot z-axis. Note that the orientation of the handle relative to the robot base does not affect the consistency of the input, i.e., if the handle is rolled to a 20° position and the surgeon presses forward away from his body, the joystick mode will produce an output that is the same as if the handle were rolled to −20° position. The output rate of the virtual joystick (velocity screw) is calculated as follows:

$$v = C \, {}^R\!Ad_S \, f, \quad \text{(Equation 1)}$$

where the measured handle force and torques f (6-DOF) in the robot frame $F_R$ are transformed by an adjoint transformation matrix ${}^R\!Ad_S$ and multiplied by a diagonal matrix C, the diagonal of which represents the factors to convert force (N) and torques (N/mm) into mm/s and rad/s. In this example C is a linear mapping, but can be extended to include non-linear and context-based transformations of the forces/torques into numerical position or velocity outputs.

The output is then transmitted to the system as a user interface input and interpreted as a rate control joystick. Note that the XYZ joystick units have to be converted from mm to pixels or mm/s to pixels/s, and depending on the surgeon's preference, and the joystick frame may need to be rotated about the horizontal axis) (90°) to align with the viewing plane in a typical eye surgery visualization setup. For a user interface according to some embodiments of the invention, only the velocity readings in a single plane (X-Y or Z-X plane) are considered in driving the mouse cursor on the display.

In some instances it is more advantageous to use the virtual joystick as a positioning device. This is accomplished by continuously integrating the velocity to generate the current position p (twist) (6DOF) at time T:

$$p_T = \int_0^T C \, {}^R\!Ad_S \, f \, dt \quad \text{(Equation 2)}$$

where dt in this case becomes the sampling period of the force/torque measurements.

The position virtual joystick capability provides a way for the surgeon to input Cartesian coordinates into the system. For example, it can be used for telestration as a cursor input to virtually draw lines on the surface of the retina in vitreoretinal surgery visualization system. The surgeon may use the virtual joystick to translate the cursor on the display over a region of interest where upon a button press event engages the drawing mode and the surgeon proceeds to draw a line by pressing on the handle in the desired directions.

In the above methods, only the force measurements are considered for inputs that generate outputs in a single plane, or single force axis. However, imprecise handle manipulation often involves a combination of torques and forces even when force-only input is desired. To enhance the sensitivity of the input and make the interaction more intuitive, especially when the surgeon is holding the instrument at a different location than where the forces/torques are resolved, the torque measurements can also be interpreted as force inputs. For example, the output velocity (V) is calculated by V=C*f+D*τ, where the D is a scaling factor that converts torques (τ) into mm/s.

The click events are implemented by monitoring forces/torques along a predefined axis with threshold values that trigger events for button down, button up, etc. A common input axis is the main tool (z-) axis. The surgeon presses on the tool in the downward direction (along the negative z-axis) with a given force for a given amount of time, which initiates a button-down click event. Alternatively, a button-up click event is also possible by applying an upward force on the tool (along the positive z-axis).

The system may include a position control mode in which the output of the joystick control is a position/rotation that is proportional to the force/torque. The position may be calculated using a scaling factor C and orientation transformation matrix ${}^R\!Ad_S$:

$$p = C \, {}^R\!Ad_S \, f. \quad \text{(Equation 3)}$$

This causes the output to "spring back" to the origin when the surgeon is no longer handling the instrument. As with the velocity output, C can be extended beyond linear mapping to include non-linear and context-based transformations of the forces/torques into numerical position or velocity outputs.

The cooperatively controlled robot may have many operating modes that the surgeon may dynamically choose to use during the operation based on the requirements of the task at hand. To facilitate rapid switching between these robot control modes, a single axis selector can be enabled with a switch (e.g., a pedal click) at which point the robot halts its motion and a predefined force/torque measurement axes is considered a selection knob, and is used to cycle back and forth through the available options. For example, applying a torque about the tool's main z-axis cycles through the user interface options (assuming z-axis is locked). A force in the clockwise direction may cycle forward through the options, and a force in the counterclockwise direction may cycle backwards through the options. The selection is set once the switch is clicked again or released. The cycling through the options is done when the force/torque input exceeds a threshold and a minimum dwell time. Although an arbitrary force/torque selection axis can be chosen for this mode, it is natural to reference a physical object such as the tool for a more intuitive input method.

Figure 6:
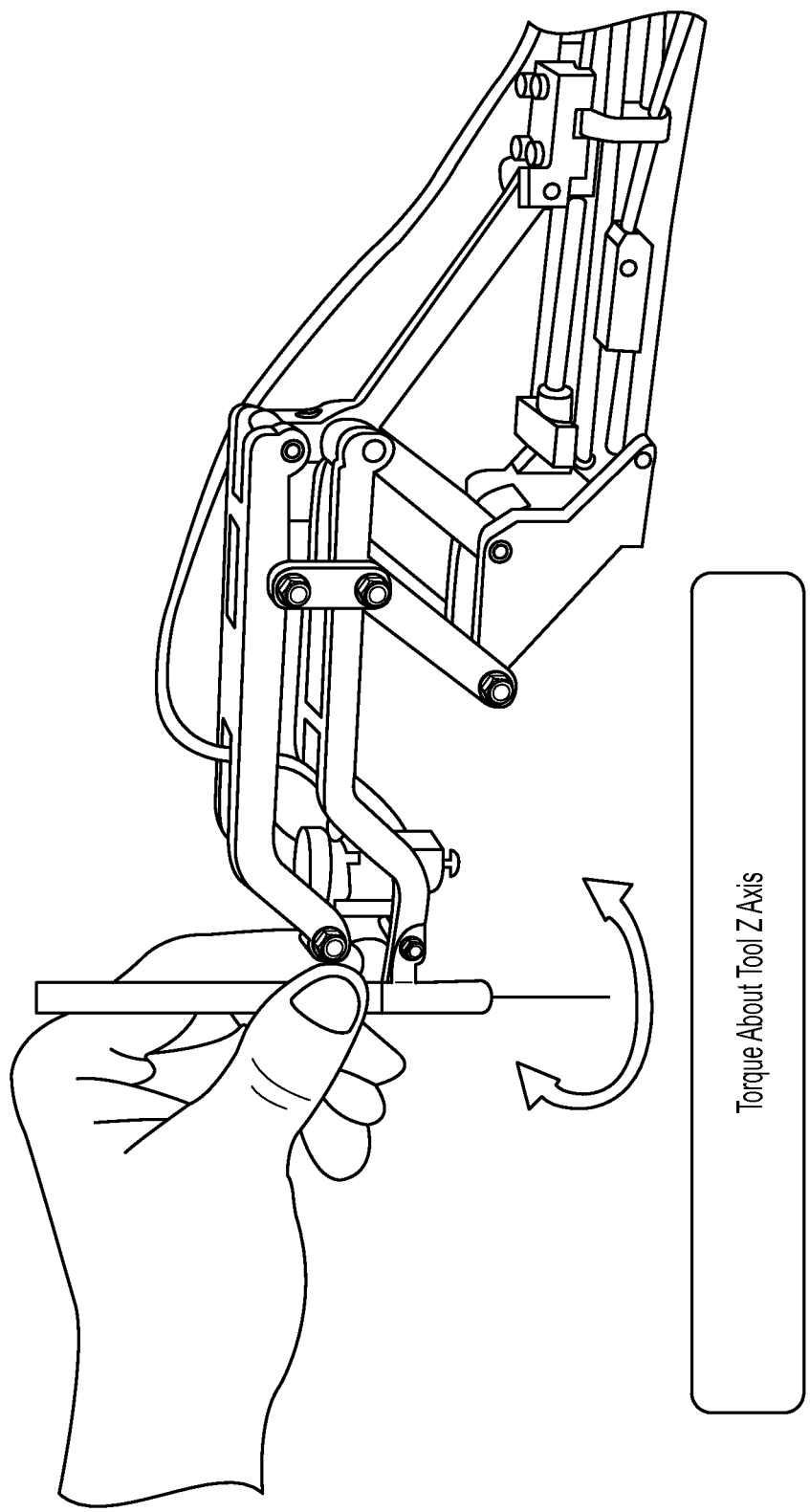
FIG. 6 illustrates how a torque may be applied about the tool's z-axis to cycle through a list of options.

According to an embodiment of the invention, a knob selection may also include a hybrid behavior where the main tool axis (see FIG. 6) is passive and encoded. The user rotates the tool about the main tool axis to cycle through the modes (no force data is considered). The system interprets the position of the rotation directly. In order to make a selection a force is applied on the tool along the tool axis triggering the pressed button down event. This behavior can also be achieved with an actuated tool axis wherein the rotation is rendered through standard admittance control.

In scenarios where the robot can safely generate motion (e.g., when it is not involved in a critical surgical task, such as during the preparation phase of a procedure), physical feedback can be generated in response to a user interface event. For example, the robot may vibrate to acknowledge a selection, a click, an error, or a mouse pointer moving over a menu item. In another example, the robot may move slightly "up" when the mouse cursor hovers over a clickable widget, and then return to its original position when the mouse cursor is off the widget. To further enhance intuitive communication, the haptic feedback may be combined with complementary aural or visual feedback. The motion of the robot is likely to induce a force on the force sensor, in which case the force/torque measurement should be disregarded for the period of the haptic feedback.

Figure 7:
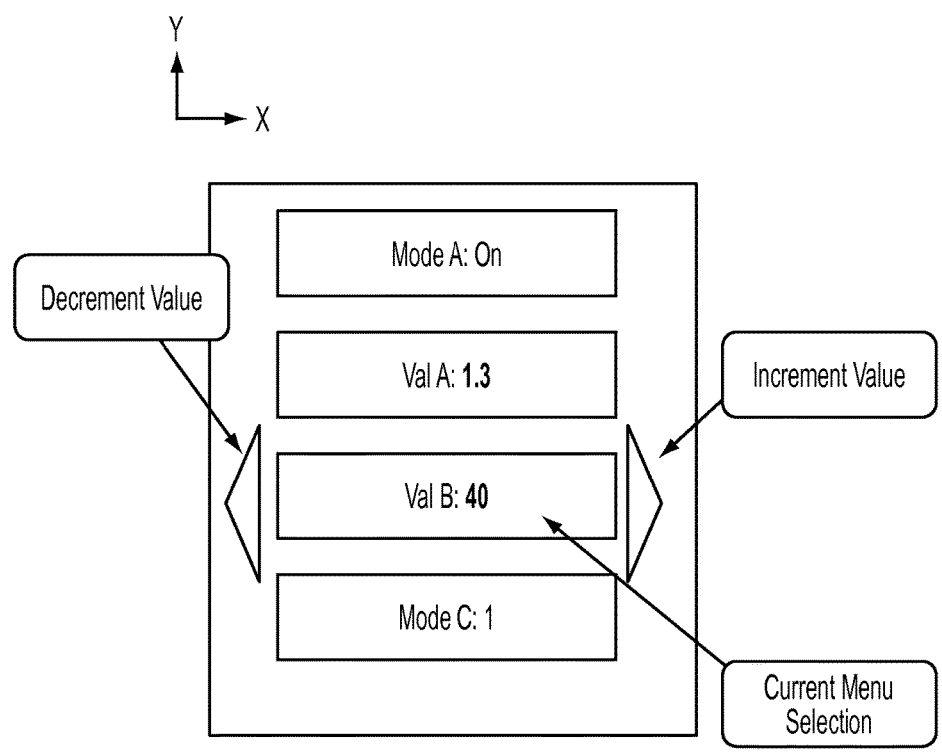
FIG. 7 shows how the single axis selector can be generalized for graphical menu navigation according to an embodiment of the invention.

The single axis selector mode can be generalized for graphical menu navigation as shown in FIG. 7. By applying a force in the y direction (positive for up, negative for down) the selections are cycled in discrete transitions. Once the desired selection is active, applying an orthogonal force (along the x-axis) adjusts the particular parameter associated with the selection. Alternatively, the parameter adjustment could be performed using the torque about the tool's z-axis.

The interaction may include a minimum force input (tolerance) so that the imprecise application of force along a particular axis does not unintentionally trigger actions based on forces along the other axes. In addition, a time delay for transitioning between options may control the cycling rate through the selections.

An alternative menu interaction includes multilayer menu widgets that can use joystick button/press events to select a menu item which opens another set of menus. For this to be an effective interaction method, visual or aural feedback may be desirable to enhance the transitions between the discrete menu items. This is similar to the iDrive from BMW and can be applied to multilayered menus, and can include the button press event for selection.

The orientation of the joystick output may be aligned with a typical hand-view for the typical surgical scenario (table aligned, or display aligned) to facilitate the surgeon's use of the system.

Surgeons often adjust the actuated zoom/pan/focus of the surgical microscope or an actuated endoscope during an operation using pedals or with their hands. Alternatively, the joystick position control mode can be mapped in the following ways to control the actuation of such a microscope without the use of such pedals or letting go of the surgical tool. A pan mode may control x-y plane translation of the microscope. A zoom made may allow for z-axis input, in which a force along the z-axis causes the microscope to zoom in or out. A focus mode may allow a surgeon to focus the microscope by applying a torque about the z-axis.

Similarly, inspection of high-resolution videos or images can be done using the same method but instead of physically controlling a microscope, the videos or images may be manipulated purely through software. A pan mode may control x-y plane translation of the viewing window over the high-resolution video or image. A zoom mode may allow the user to magnify a section of the image, with a force along the z-axis causing the microscope to zoom in or out. The select function cycles through a list of available images in response to a torque about the z-axis. In addition to videos and images, audio data streams may also be inspected an manipulated using the cooperatively controlled robot in the user interface control mode. The robot may also be used inspect medical data such as a patient's vitals, an electroencephalogram (EEG), an electrocardiogram (EKG), or other images that are created using patient data.

A 3-D model inspection mode allows the surgeon to manipulate the view of a 3-D model with the 6-DOF joystick input, directly mapping to the standard 3-D viewing, similar to 3-D space mouse interaction.

In the 3-D model alignment mode for augmented reality, the joystick can be used to perform pose adjustments to a virtual anatomical model that is superimposed on top of the view of the surgical area. This initial alignment step is often helpful in the registration of models with visual data in augmented reality applications. An example is a 3-D model of a kidney with a tumor derived from preoperative images that is used during the operation for navigation.

The surgical system described herein may be used for auxiliary manipulator control. According to an embodiment of the invention, more than one robotic manipulator is used in the operating room. The system may have a bimanual EyeRobot setup, or may be a combination of an EyeRobot and an actuated endoscope holding robot. With the ability to use the cooperatively controlled robot as a joystick, a teleoperation control scheme is possible in which one robot is in the joystick mode, which is used to position the other robot. This can provide a finer level of control, or provide the necessary control input for a teleoperated robot.

The embodiments described above disclose a cooperatively controlled robot. Alternatively, a surgical system user interface may be configured to be used with a cooperatively controlled robot. The surgical system user interface may include a control system adapted to communicate with a robotic actuator assembly and a force sensor of the cooperatively controlled robot. The surgical system user interface may also include an output system in communication with the control system, wherein the control system is configured to receive an instruction from a user to switch from a robot control mode into a user interface control mode, and wherein the control system is configured to receive from a force sensor an indication of at least one of a force and a torque applied to a tool and manipulate the output system based on the indication. The surgical system user interface, in conjunction with a cooperatively controlled robot, may be configured to perform all of the functions described above with regard to the cooperatively controlled robot.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A cooperatively controlled robot, comprising:
   a robotic actuator assembly comprising a tool holder and a force sensor;
   a control system adapted to communicate with said robotic actuator assembly and said force sensor; and
   an output system in communication with said control system,
   wherein said tool holder is configured to receive a tool to be manipulated by a user,
   wherein said control system is configured to receive an instruction from a user to switch from a robot control mode into a user interface control mode,
   wherein said force sensor is configured to measure at least one of a force and a torque applied to said tool by said user, and
   wherein said control system, in said user interface control mode, is configured to receive an indication of said at least one of a force and a torque applied to said tool by said user and manipulate said output system based on said indication while disabling motion of said robot.

2. A cooperatively controlled robot according to claim 1, further comprising:
   a microphone in communication with said control system, wherein said instruction from a user to switch from a robot control mode into a user interface control mode comprises a verbal signal detected by said microphone.

3. A cooperatively controlled robot according to claim 1, further comprising:
   a pedal in communication with said control system, wherein said instruction from a user to switch from a robot control mode into a user interface control mode comprises a push or a release of said pedal.

4. A cooperatively controlled robot according to claim 1, further comprising:
   a physical button in communication with said control system, wherein said instruction from a user to switch from a robot control mode into a user interface control mode comprises a command received through said physical button.

5. A cooperatively controlled robot according to claim 1, further comprising:
   a second output system in communication with said control system, wherein said instruction from a user to switch from a robot control mode into a user interface control mode comprises a command received through a user interface of said second output system.

6. A cooperatively controlled robot according to claim 1, wherein said output system is an audio system.

7. A cooperatively controlled robot according to claim 1, wherein said output system is a visual display system.

8. A cooperatively controlled robot according to claim 7, wherein said control system is configured to manipulate said visual display system by changing a position of a cursor based on said indication.

9. A cooperatively controlled robot according to claim 7, wherein said control system is configured to manipulate said visual display system by changing a velocity of a cursor based on said indication.

10. A cooperatively controlled robot according to claim 7, wherein said visual display system is configured to display an image, and wherein said control system is configured to manipulate said image based on said indication.

11. A cooperatively controlled robot according to claim 10, wherein said image is created using data from a patient.

12. A cooperatively controlled robot according to claim 7, wherein said visual display system is configured to display an image, and wherein said control system is configured to manipulate said visual display system by zooming into or out of said image based on said indication.

13. A cooperatively controlled robot according to claim 1, wherein said output system is a second robotic actuator assembly.

14. A cooperatively controlled robot according to claim 1, wherein said output system is a microscope.

15. A cooperatively controlled robot according to claim 1, wherein said output system is a light source.

16. A cooperatively controlled robot according to claim 1, wherein said control system is configured to manipulate said output system by browsing through a list of parameters and selecting a parameter based on said indication.

17. A cooperatively controlled robot according to claim 1, wherein said control system is configured to perform a button press function on a condition that said force is exerted along a predetermined axis and exceeds at least one of a predetermined duration and magnitude.

18. A cooperatively controlled robot according to claim 1, wherein said tool is a surgical instrument.

19. A cooperatively controlled robot according to claim 1, wherein said tool is a joystick tool.

20. A surgical system user interface for a cooperatively controlled robot, comprising:
   a control system adapted to communicate with a robotic actuator assembly and a force sensor; and
   an output system in communication with said control system,
   wherein said control system is configured to receive an instruction from a user to switch from a robot control mode into a user interface control mode, and
   wherein said control system, in said user interface control mode, is configured to receive from a force sensor an indication of at least one of a force and a torque applied to a tool by a user and manipulate said output system based on said indication while disabling motion of said robot.

* * * * *